(12) United States Patent
Negi et al.

(10) Patent No.: US 10,058,263 B2
(45) Date of Patent: Aug. 28, 2018

(54) NEURAL INTERFACE

(71) Applicant: University of Utah Research Foundation, Salt Lake City, UT (US)

(72) Inventors: Sandeep Negi, Salt Lake City, UT (US); Rajmohan Bhandari, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 229 days.

(21) Appl. No.: 14/667,154

(22) Filed: Mar. 24, 2015

(65) Prior Publication Data

US 2015/0305643 A1    Oct. 29, 2015

Related U.S. Application Data

(60) Provisional application No. 61/969,666, filed on Mar. 24, 2014.

(51) Int. Cl.
*A61B 5/0478* (2006.01)
*A61B 5/04* (2006.01)
*A61B 5/00* (2006.01)

(52) U.S. Cl.
CPC ........ *A61B 5/0478* (2013.01); *A61B 5/04012* (2013.01); *A61B 5/6846* (2013.01); *A61B 2562/125* (2013.01); *A61B 2562/227* (2013.01)

(58) Field of Classification Search
CPC .. A61B 5/0478; A61B 5/6846; A61N 1/0529; A61N 1/0531; A61N 1/0534
See application file for complete search history.

(56) References Cited

U.S. PATENT DOCUMENTS 3,986,495 A * 10/1976 Miller ............... A61B 5/04282
                                              128/908
7,212,851 B2 * 5/2007 Donoghue ......... A61B 5/04001
                                              600/378
(Continued)

FOREIGN PATENT DOCUMENTS

WO    WO2014/067963        5/2014

OTHER PUBLICATIONS

Thongpang et al, A Micro-Electrocorticography Platform and Deployment Strategies for chronic BCI Applications; Clin EEG Neurosci; National Institutes of Health; Oct. 2011; pp. 259-265; vol. 42 Issue 4.

(Continued)

*Primary Examiner* — Lee S Cohen
(74) *Attorney, Agent, or Firm* — Thorpe North & Western, LLP

(57) ABSTRACT

Technology for a neural interface is described. The neural interface can include an intracranial electrode grid operable to detect neural activity. The neural interface can include a subcutaneous microelectronic signal processing unit operable to process the neural activity in order to obtain digital neural activity information. The neural interface can include a cable connecting the intracranial electrode grid and the subcutaneous microelectronic signal processing unit. The neural interface can include a wired connector attached to the subcutaneous microelectronic signal processing unit that is operable to transmit the digital neural activity information from the subcutaneous microelectronic signal processing unit to an external signal processing device.

15 Claims, 7 Drawing Sheets

(56) References Cited

U.S. PATENT DOCUMENTS

| | | | |
|---|---|---|---|
| 7,326,649 | B2 | 2/2008 | Rodger et al. |
| 8,090,446 | B2 | 1/2012 | Fowler et al. |
| 8,423,143 | B2 | 4/2013 | Bartic et al. |
| 8,560,041 | B2 | 10/2013 | Flaherty et al. |
| 8,666,471 | B2 | 3/2014 | Rogers et al. |
| 8,870,857 | B2 * | 10/2014 | Seymour ............ A61B 5/0084 600/342 |
| 8,977,367 | B2 * | 3/2015 | Elahi ................ A61N 1/05 607/116 |
| 9,107,592 | B2 * | 8/2015 | Litt .................. A61B 5/0031 |
| 9,486,168 | B2 * | 11/2016 | Bonmassar .......... A61N 1/0531 |
| 2002/0022872 | A1 | 2/2002 | Gielen et al. |
| 2005/0197685 | A1 * | 9/2005 | Russell ............ A61B 5/04282 607/115 |
| 2007/0213786 | A1 | 9/2007 | Sackellares et al. |
| 2007/0265489 | A1 | 11/2007 | Fowler et al. |
| 2010/0145176 | A1 | 6/2010 | Himes |
| 2011/0092842 | A1 | 4/2011 | Decaria et al. |
| 2011/0213222 | A1 | 9/2011 | Leyde et al. |
| 2011/0251512 | A1 * | 10/2011 | Fink .................. A61B 5/0488 600/546 |
| 2012/0245481 | A1 | 9/2012 | Blanco et al. |
| 2012/0296444 | A1 | 9/2012 | Greenberg et al. |
| 2013/0072775 | A1 | 3/2013 | Rogers et al. |
| 2013/0144365 | A1 * | 6/2013 | Kipke ............... A61B 5/04001 607/93 |
| 2014/0058239 | A1 | 2/2014 | Joshi et al. |
| 2017/0035316 | A1 * | 2/2017 | Kuzniecky .......... A61B 5/0478 |
| 2017/0049398 | A1 * | 2/2017 | Hirata ............... A61B 5/6868 |

OTHER PUBLICATIONS

Chang et al, A Wireless and Batteryless Microsystem With Implantable Grid Electrode/3-Dimensional Probe Array for EcoG and Extracellular Neural Recording in Rats; Sensors; Apr. 8, 2013; pp. 4624-4639; vol. 13 Issue 4.

Rothschild, Neuroengineering Tools/Applications for Bidirectional Interfaces, Brain-Computer Interfaces, and Neuroprosthetic Implants—A Review of Recent Progress; Frontiers in Neuroengineering; Oct. 15, 2010; pp. 1-15; vol. 3 Article 112.

Xie et al, Long-Term Bilayer Encapsulation Performance of Atomic Layer Deposited Al2O3 and Parylene C for Biomedical Implantable Devices; IEEE Transactions on Biomedical Engineering; Jun. 6, 2013; vol. 60 Issue 10.

Van Gompel et al.; "Phase I Trial: Safety and Feasibility of Intracranial Electroencephalography Using Hybrid Subdural Electrodes Containing Macro- and Microelectrode Arrays"; Neurosurgical Focus Journal; (Sep. 2008); 11 pages; vol. 25, No. 3; E23; <doi: 10.3171/FOC/2008/25/9/E23 >.

* cited by examiner

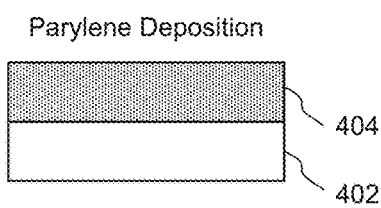
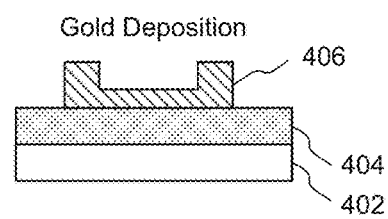
FIG. 4A  FIG. 4B
 Parylene   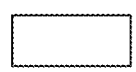 Substrate    Gold
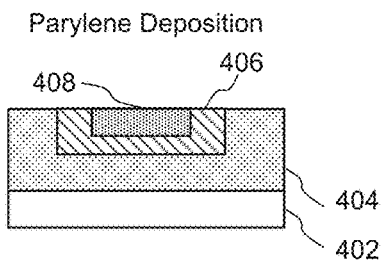
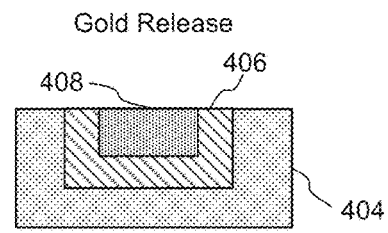
FIG. 4C  FIG. 4D

NEURAL INTERFACE

RELATED APPLICATIONS

This application claims the benefit and hereby incorporates by reference U.S. Provisional Patent Application Ser. No. 61/969,666, filed Mar. 24, 2014, and entitled "Polymer Based Thin Film Technology for Surface Electrode Arrays (ECoG) and Flexible Interconnections".

BACKGROUND

A brain-machine interface (BMI) or a brain-computer interface (BCI) is a direct communication pathway between a brain and an external device. BMIs can be used to assist, augment and/or repair human cognitive or sensory-motor functions. In one example, a BMI can include an array of electrodes that are invasively or partially invasively spread over an area of a subject's brain. The array of electrodes can obtain neural signal information from the subject's brain. The neural signal information can be communicated to the external device for analysis.

Electrocorticography (ECoG), or intracranial electroencephalography (iEEG), is a practice of using electrodes placed directly on an exposed surface of a brain in order to measure electrical potentials (or electrical activity) from the brain's cerebral cortex. The electrodes can be referred to as an intracranial electrode grid. Since a surgical incision into the skull is performed to implant the intracranial electrode grid over the brain, ECoG involves an invasive surgical procedure. In one example, electrical measurements from the ECoG can be used to identify epileptogenic zones (i.e., regions of the brain that generate epileptic seizures), which can be subsequently removed during surgery.

ECoG is growing in importance for brain-machine interfaces (BMI), and is a fundamental research tool for the investigation of long-range neural circuitry and synchronization. For BMI applications, the development of large area, high-resolution ECoG electrode grids is desirable. Although ECoG recordings have been found useful for epilepsy monitoring and for effectively controlling cursor movements at the brain-machine interface (BMI), traditional ECoG recordings are occasionally complicated by hemorrhage, infection, infarction, etc.

Traditional ECoG electrode grids can include a polydimethylsiloxane (PDMS) sheet with embedded platinum studs connected to a recording apparatus. These traditional ECoG grids can suffer from several disadvantages such that continued improvements in ECoG grids are desirable.

SUMMARY

Briefly, and in general terms, the invention is directed to a neural interface. In one embodiment, the neural interface can include an intracranial electrode grid operable to detect neural activity; a subcutaneous microelectronic signal processing unit operable to process the neural activity in order to obtain digital neural activity information; a cable connecting the intracranial electrode grid and the subcutaneous microelectronic signal processing unit; and a wired connector attached to the subcutaneous microelectronic signal processing unit that is operable to transmit the digital neural activity information from the subcutaneous microelectronic signal processing unit to an external signal processing device.

In one embodiment, a system for detecting and processing neural activity is provided. The system can include an integrated macro and micro electrocorticography (ECoG) array system operable to detect neural activity; a subcutaneous microelectronic signal processing unit operable to process the neural activity in order to obtain digital neural activity information; a cable connecting the integrated macro and micro ECoG array system and the subcutaneous microelectronic signal processing unit; a single pigtail connector attached to the subcutaneous microelectronic signal processing unit; and an external signal processing device that is operable to receive the digital neural activity information from the subcutaneous microelectronic signal processing unit via the pigtail connector.

In one embodiment, a method for manufacturing a neural interface is provided. The method can include creating an intracranial electrode grid by inserting a defined number of interconnections between a first polymer layer and a second polymer layer; attaching the intracranial electrode grid to a first surface of a subcutaneous microelectronic signal processing unit, wherein bond pads on the intracranial electrode grid are configured to attach with bond pad spacing on the subcutaneous microelectronic signal processing unit; and attaching a wired connector to a second surface of the subcutaneous microelectronic signal processing unit.

There has thus been outlined, rather broadly, the more important features of the disclosure so that the detailed description that follows may be better understood, and so that the present contribution to the art may be better appreciated. Other features of the disclosure will become clearer from the following detailed description of the disclosure, taken with the accompanying drawings and claims, or may be learned by the practice of the disclosure.

BRIEF DESCRIPTION OF THE DRAWINGS

Features and advantages of the disclosure will be apparent from the detailed description which follows, taken in conjunction with the accompanying drawings, which together illustrate, by way of example, features of the disclosure; and, wherein:

FIGS. 4A-4D illustrate fabrication of an integrated intracranial electrode grid and in accordance with an example;

Figure 1A:
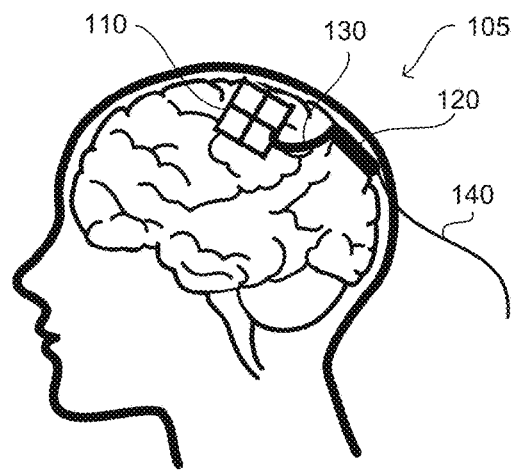
FIGS. 1A-1C illustrate a neural interface in accordance with an example.

Reference will now be made to the exemplary embodiments illustrated, and specific language will be used herein to describe the same. It will nevertheless be understood that no limitation of the scope of the invention is thereby intended.

DETAILED DESCRIPTION

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular examples only and is not intended to be limiting. The same reference numerals in different drawings represent the same element. Numbers provided in flow charts and processes are provided for clarity in illustrating steps and operations and do not necessarily indicate a particular order or sequence.

Example Embodiments

An initial overview of technology embodiments is provided below and then specific technology embodiments are described in further detail later. This initial summary is intended to aid readers in understanding the technology more quickly and is not intended to identify key features or essential features of the technology, nor is it intended to limit the scope of the claimed subject matter.

Reference throughout this specification to "an example" means that a particular feature, structure, or characteristic described in connection with the example is included in at least one invention embodiment. Thus, appearances of the phrases "in an example" in various places throughout this specification are not necessarily all referring to the same embodiment.

As used in this specification and the appended claims, the singular forms "a," "an" and "the" include plural referents unless the context clearly dictates otherwise. Thus, for example, reference to "a layer" includes a plurality of such layers.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms." Furthermore it is to be understood that in this specification, the recitation of a numerical value in connection with the term "about" is also intended to provide support for the actual numerical value in and of itself apart from the term "about". Thus for example, the recitation of "about 30" also includes express support for the plain numerical value of "30".

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and invention examples may be referred to herein along with alternatives for the various components thereof. It is understood that such embodiments, examples, and alternatives are not to be construed as defacto equivalents of one another, but are to be considered as separate and autonomous representations of various invention embodiments.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

The current technology includes a neural interface that employs biocompatible and electrodes of a reduced size on a flexible substrate in order to reduce complications and facilitate long term ECoG recordings. The neural interface described herein is a thin, highly flexible, biocompatible, reliable and affordable neural interface that links the intracranial electrode grid (e.g., an ECoG electrode grid) to implantable electronics. In one example, the neural interface can be applicable to electrocorticography (ECoG) for the diagnosis and treatment of intractable epilepsy.

FIG. 1A illustrates an exemplary neural interface 105. The neural interface 105 can include an intracranial electrode grid 110 operable to detect neural activity. The intracranial electrode grid 110 can be an electrocorticography (ECoG) array system. In other words, the intracranial electrode grid can include an array of electrodes used for ECoG. The intracranial electrode grid 110 can include 128 signal channels, although other numbers of channels can be used (e.g. most commonly 8 to 1024). The 128 signal channels can correspond to 128 locations or sites on the brain for which electrical recordings can be captured at a defined sampling rate. In other words, the 128 signal channels can be used to convey neural activity information for the 128 sites on a user's brain. The intracranial electrode grid 110 can be an integrated macro and micro ECoG array system. Therefore, the 128 signal channels can be for a mixture of macro signal channels/sites and micro signal channels/sites (i.e., a total number of macro signal channels and micro signal channels is equal to 128). The neural activity detected by the intracranial electrode grid 110 can include ECoG measurements (or measurements of electrical activity from the cerebral cortex). In one example, the intracranial electrode grid 110 can be inserted within a cranial cavity (i.e., between the brain and the skull) of the user.

In one configuration, the intracranial electrode grid 110 can include 128 channels or sites. In this configuration, the intracranial electrode grid 110 can include four four-by-four micro channels/sites and 64 macro channels/sites. The four four-by-four micro channels/sites can be approximately 50 micrometers (μm) in size and spaced at approximately 400 μm, and the 64 macro channels/sites can be approximately 2000 μm in size and spaced at approximately 10,000 μm. In addition, the intracranial electrode grid 110 can be comprised of a polymer, such as parylene, and be approximately 15 micrometers (μm) to 25 μm in thickness.

In one alternative, the electrode grid can be formed on a bi-layer substrate including an outer ion barrier and an inner adjacent moisture barrier. For example, the outer ion barrier can be a polymer such as parylene-C, polyimide or the like, while the moisture barrier can be an aluminum oxide. In comparison to PDMS, Parylene-C has a low water absorption rate of 0.1% for 24 h, low dielectric constant of 3.15 at 60 Hz, USP Class VI biocompatibility, chemical inertness, and is also an excellent ion barrier. Failure of parylene-C has been reported due to moisture diffusion and interface contamination. Atomic layer deposited (ALD) $Al_2O_3$ is an excellent moisture barrier with water vapor transmission rate (WVTR) of $10^{-6}$ g/m$^2$ day. These films are conformal and pin-hole free. Water is known to corrode $Al_2O_3$; therefore, $Al_2O_3$ works as an inner moisture barrier while parylene-C functions as an external barrier to ions and prevents contact of the $Al_2O_3$ with liquid water, and to inhibit the transport of reactants/products involved with corrosion. Such a bi-layer coating lasts at least three times longer than parylene-C coated samples at 80° C. The results suggests that combining A and P leads to a robust polymer for chronic biomedical implants.

The neural interface 105 can include a subcutaneous microelectronic signal processing unit 120 operable to process the neural activity collected by the intracranial electrode grid 110. The subcutaneous microelectronic signal processing unit 120 can be inserted or implanted between the skull and the skin (i.e., between a cranium and a cutaneous layer). Therefore, the subcutaneous microelectronic signal processing unit 120 can be in a different layer or location as compared to the intracranial electrode grid 110. The subcutaneous microelectronic signal processing unit 120 can include computer circuitry (e.g., a digital processor board) to amplify the neural activity detected by the intracranial electrode grid 110, digitize the neural activity to obtain digital neural activity information, and multiplex the digital neural activity information prior to transmission of the digital neural activity information. The digital neural activity information can refer to a digital representation of a user's brain electrical activity. In one example, the neural interface 105 can include housing to encapsulate the subcutaneous microelectronic signal processing unit 120. In another example, the subcutaneous microelectronic signal processing unit 120 can include shock protection in case of neural interface failure. Therefore, electrical problems that occur in the subcutaneous microelectronic signal processing unit 120 may not cause harm to the user's brain.

The neural interface 105 can include a cable 130 that connects the intracranial electrode grid 110 and the subcutaneous microelectronic signal processing unit 120. For example, the cable 130 can be a thin, highly flexible, biocompatible micro-ribbon cable. The cable 130 can transport neural activity collected by the intracranial electrode grid 110 to the subcutaneous microelectronic signal processing unit 120 for processing. In one example, the cable 130 can be constructed using a polymer, such as parylene.

The neural interface 105 can include a wired connector 140 that is attached to the subcutaneous microelectronic signal processing unit 120. The wired connector 140 can transmit the digital neural activity information from the subcutaneous microelectronic signal processing unit 120 to an external signal processing device (not shown in FIG. 1A). In one example, the wired connector 140 can be a pigtail connector or a pigtail wire/cable that exits the cutaneous layer and is connectable to the external signal processing device. In other words, the wired connector 140 can carry the digital neural activity information from the subcutaneous microelectronic signal processing unit 120 through the user's skin to the external signal processing device. In one configuration, the wired connector 140 can be a single percutaneous flexible cable (or pigtail) that can connect to the external signal processing device.

In one example, the subcutaneous microelectronic signal processing unit 120 can include active electronics, such as a digital processor board (DPB), that allows for a relatively long wired connector 140 (or cable) to attach the subcutaneous microelectronic signal processing unit 120 to the external signal processing device. As a result, the digital neural activity information (e.g., broadband signals that indicate field and spike potential) can be transmitted to the external signal processing device. The DPB in the subcutaneous microelectronic signal processing unit 120 can use a printed circuit board (PCB), wherein the PCB can have an area of less than approximately one square inch and a thickness of less than approximately four millimeters (mm). The intracranial electrode grid 110 can be connected to a bottom surface of the PCB using wire bonds. An amplifier application-specific integrated circuit (ASIC) can be attached directly opposite to the wire bonds on a top surface of the PCB. The amplifier ASIC can mate with pad spacing that is substantially identical to a wire bond area in order to reduce an amount of signal routing.

The wired connector 140 (i.e., the pigtail) can be connected to the top surface of the PCB on an opposite end from the wire bonds. In one example, the wired connector 140 can be connected to the top surface of the PCB using soldering. The wired connector 140 can use a standard electroencephalography (EEG) lead with 16 connections, as opposed to the 128 connections that would be used to transfer all of the electrode signals collected from the 128 channel intracranial electrode grid 110 in traditional devices that do not utilize the subcutaneous microelectronic signal processing unit 120.

In one example, the PCB can include a controller ASIC that selects channels on the amplifier ASIC, controls analog-to-digital converters (ADC) on the PCB, and packetizes the digital neural activity information for transmission from the subcutaneous microelectronic signal processing unit 120 to the external signal processing device. The PCB can incorporate through-hole vias (i.e., the through-hole paths to the other surface) of a reduced size between the amplifier ASIC and the wire bond area.

In one example, the subcutaneous microelectronic signal processing unit 120 (e.g., the DPB) can be coated with biocompatible materials, such as silicone and parylene. The subcutaneous microelectronic signal processing unit 120 can be encapsulated or encased within a housing to allow the subcutaneous microelectronic signal processing unit 120 to be implanted. In one example, the housing can include a titanium can. By digitizing the neural activity information on the subcutaneous microelectronic signal processing unit 120 (e.g., the DPB), a simplified connection with a reduced number of connections can be used.

The neural interface 105 can provide improvements in applied neuroprosthetic instrumentation. For example, the neural interface 105 can provide greater flexibility to minimize tethering forces, 128 signal channels, and sufficient bandwidth resolution to record local field potential (LFP) data from the intracranial electrode grid 110. The LFP data can be for electrophysiological signals that are generated in a certain volume of nervous tissue. The neural interface 105 can provide a number of additional advantages. For example, the intracranial electrode grid 110 can be perforated to allow diffusion. The perforations can range in size, but can often vary from 5-50 μm perforations, although other sizes may be suitable. The intracranial electrode grid 110 can have integrated macro and arrays (4×4) of micro channels. The intracranial electrode grid 110 can be constructed using parylene (e.g., parylene C). The intracranial electrode grid 110 can be relatively thin (e.g., 15-25 μm) and ultra-flexible to follow a surface profile of the cerebral cortex while retaining mechanical robustness. Since the intracranial electrode grid 110 can be constructed using thin film parylene, the electrodes are anticipated to adhere to the surface of the cerebral cortex relatively well due to surface tension.

Other advantages of the neural interface 105 can include a utilization of a single wired connector (or a single pigtail wire) for the 128 signal channels, which can reduce a size of an opening or incision on the user's head. In addition, the single pigtail can minimize chances of infection (e.g., due to less incision) and tethering forces. The neural interface 105 can include patient protection circuitry in case of component failure on the subcutaneous microelectronic signal processing unit 120. The patent protection circuitry can limit an amount of charge that can be injected into an electrode to below a defined threshold, wherein the defined threshold can have been previously shown to cause tissue damage. In addition, the intracranial electrode grid 110 can be located closer to the subcutaneous microelectronic signal processing unit 120 (which can be encased in a titanium housing and mounted on the user's skull), which can result in reduced noise levels.

In one example, the neural device 105 can allow self-test of channel impedance for real time marking of deactivated/bad channels. The neural interface 105 can work with post-processing software solutions (e.g., software solutions that execute on the external signal processing device) that indicate invalid channels in the intracranial electrode grid 110 based on correlation of data on neighboring channels. For applications in BMI, these interfaces and approaches can provide high fidelity ECoG electrode grids with electrode size and pitch that optimizes spatiotemporal resolution and signal-to-noise ratio (SNR).

In one example, localized application of carboxymethyl cellulose (CMC) or polyethylene glycol (PEG) can allow temporary or localized stiffening of the thin polymer film of the intracranial electrode grid 110 during implantation. The localized stiffening can be useful because access to some areas of the brain necessitates an increased degree of stiffness during placement. After placement of the intracranial electrode grid 110 has occurred, the CMC can degrade and leave a flexible electrode grid.

In one example, the intracranial electrode grid 110 can include loop holes along an out edge to accommodate suturing of the intracranial electrode grid 110 to the dura (i.e., a thick membrane that surrounds the brain) to reduce movement relative to the cerebral cortex. The intracranial electrode grid 110 can also be perforated to allow diffusion and cerebrospinal fluid (CSF). In addition, the intracranial electrode grid 110 can have additional self-test leads that allow marking and software elimination of faulty or unused channels on the intracranial electrode grid 110.

In one example, the neural interface 105 can provide clinicians with freedom to specify customized electrode grid geometries and layouts (e.g., size and location of sites/channels) based on a patient's profile. The intracranial electrode grid 110 can have recording, stimulation, and impedance measuring capabilities. The subcutaneous microelectronic signal processing unit 120 can include custom multiplexing ASIC electronics/DPB that is capable of 128-channel recordings at 16-bit resolution, as well as a relatively fast settle capability (e.g., for stimulation option). In one example, the subcutaneous microelectronic signal processing unit 120 (e.g., the DPB) can be approximately 1.0×0.75 inches. A noise performance of the subcutaneous microelectronic signal processing unit 120 can operate in between 20-30 micro volts (μV) peak to peak. In addition, the subcutaneous microelectronic signal processing unit 120 can include protection circuitry to prevent shock in case of device failure. The protection circuitry can include a capacitor isolation circuit in between the amplifier ASIC and the electrode input pads, wherein the capacitor isolation circuit can include a 0.047 micro farad (μF) capacitor and a 10 mega ohm (MΩ) resistor.

Figure 1B:
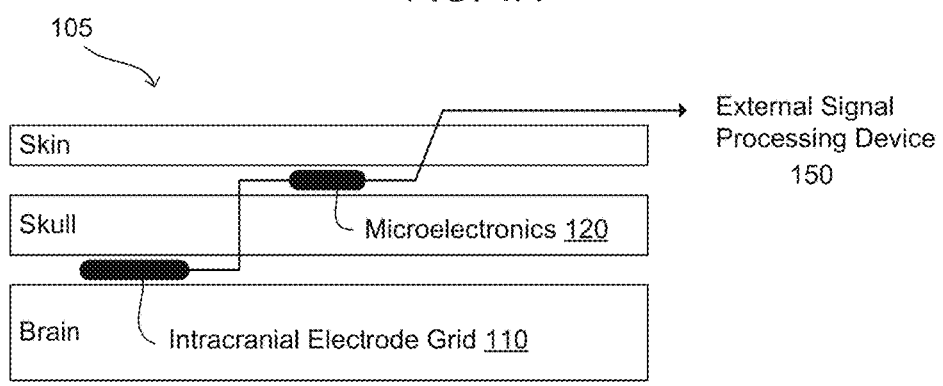

FIG. 1B illustrates an exemplary neural interface 105. The neural interface 105 can enable the recording and communication of brain electrical activity. The neural interface 105 can include an intracranial electrode grid 110 that is operable to detect neural activity. The intracranial electrode grid 110 can be positioned in between a user's brain and skull. The intracranial electrode grid 110 can be connected to a subcutaneous microelectronic signal processing unit 120 (or microelectronics). The subcutaneous microelectronic signal processing unit 120 can be positioned in between the user's skull and skin. The subcutaneous microelectronic signal processing unit 120 can process the neural activity in order to obtain digital neural activity information. The subcutaneous microelectronic signal processing unit 120 can transmit the digital neural activity information to an external signal processing device 150. The external signal processing device 150 can be located outside the skin. The external signal processing device 150 can perform additional processing on the digital neural activity information. In addition, the external signal processing device 150 can include software applications to interpret the digital neural activity information (e.g., detect abnormalities).

Figure 1C:
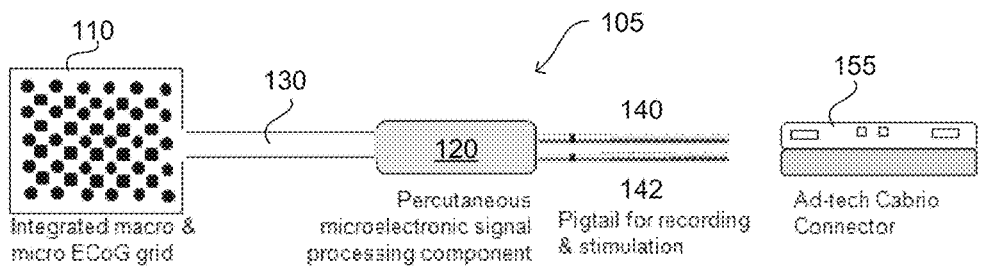

FIG. 1C illustrates an exemplary neural interface 105. The neural interface 105 can include an intracranial electrode grid 110. The intracranial electrode grid 110 can also be referred to as an integrated macro and micro electrocorticography (ECoG) grid due to a mixture of macro and micro channels or sites in the intracranial electrode grid 110. The intracranial electrode grid 110 can be connected to a subcutaneous microelectronic signal processing unit 120 via a cable 130 (e.g., a micro-ribbon cable). The subcutaneous microelectronic signal processing unit 120 can be referred to as a percutaneous microelectronic signal processing component. The subcutaneous microelectronic signal processing unit 120 can be connected to a wired connector 140 (e.g., a pigtail wire). The wired connector 140 can transmit digital neural activity information from the subcutaneous microelectronic signal processing unit 120. The wired connector 140 can attach the subcutaneous microelectronic signal processing unit 120 to a connection system 155, which can enable a transmission of the digital neural activity information from the subcutaneous microelectronic signal processing unit 120 to an external signal processing device (e.g., an external neural signal processor) via the wired connector 140 and the connection system 155.

In one example, the wired connector 140 can enable recording of the user's neural activity because the wired connector 140 transmits the digital neural activity information to the external signal processing device. In one configuration, an additional wired connector 142 can be attached to the subcutaneous microelectronic signal processing unit 120. The additional wired connector 142 can enable stimulation of the intracranial electrode grid 110. In other words, the additional wired connector 142 can send electrical impulses from the external signal processing system to the intracranial electrode grid 110 in order to stimulate the user's brain. Therefore, the wired connector 140 (e.g., a first pigtail wire) can be used for recording and the additional wired connector 142 (e.g., a second pigtail wire) can be used for stimulation.

Figure 2A:
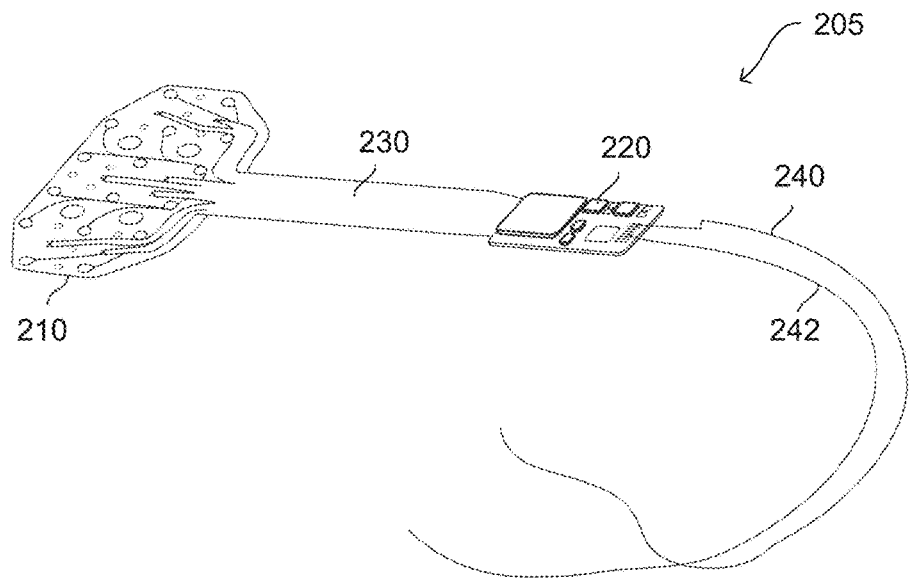
FIGS. 2A-2B illustrate a neural interface in accordance with an example.

FIG. 2A illustrates an exemplary neural interface 205. The neural interface 205 can include an intracranial electrode grid 210 operable to detect neural activity, a subcutaneous microelectronic signal processing unit 220 operable to process the neural activity in order to obtain digital neural activity information, a cable 230 that connects the intracranial electrode grid 210 and the subcutaneous microelectronic signal processing unit 220, a first wired connector 240 (e.g., a first pigtail wire) to enable the neural activity to be recorded, and a second wired connector 242 (e.g., a second pigtail wire) to enable a user's brain to be stimulated. Therefore, the neural interface 205 can provide recording and stimulation capabilities, as well as impedance measuring capabilities, for sub chronic use.

Figure 2B:
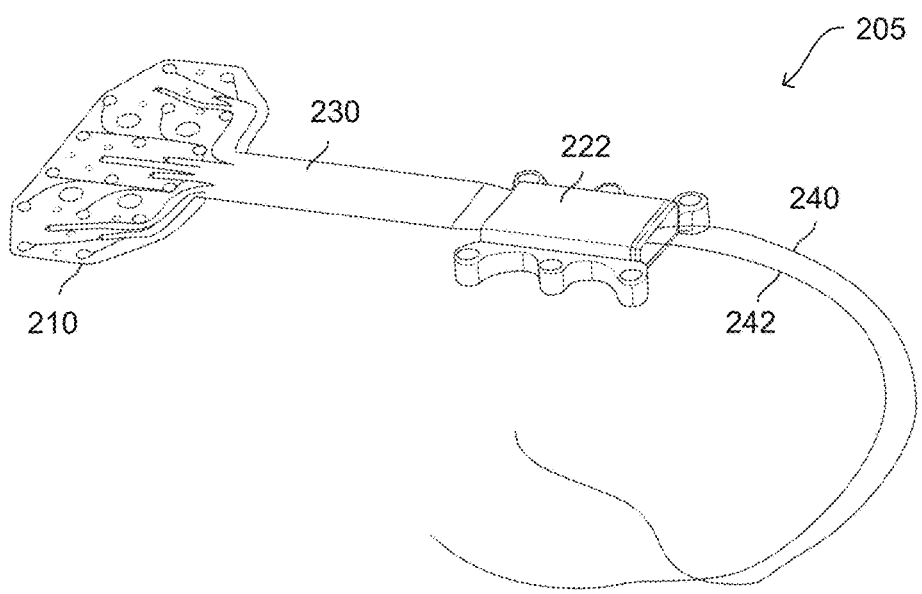

FIG. 2B illustrates an exemplary neural interface 205. The neural interface 205 can include an intracranial electrode grid 210, a housing 222 that encapsulates a subcutaneous microelectronic signal processing unit (not shown in FIG. 2B), a cable 230, a first wired connector 240 (e.g., a first pigtail), and a second wired connector 242 (e.g., a second pigtail). The housing 222 can enable the subcutaneous microelectronic signal processing unit to be more easily inserted in a patient.

Figure 3A:
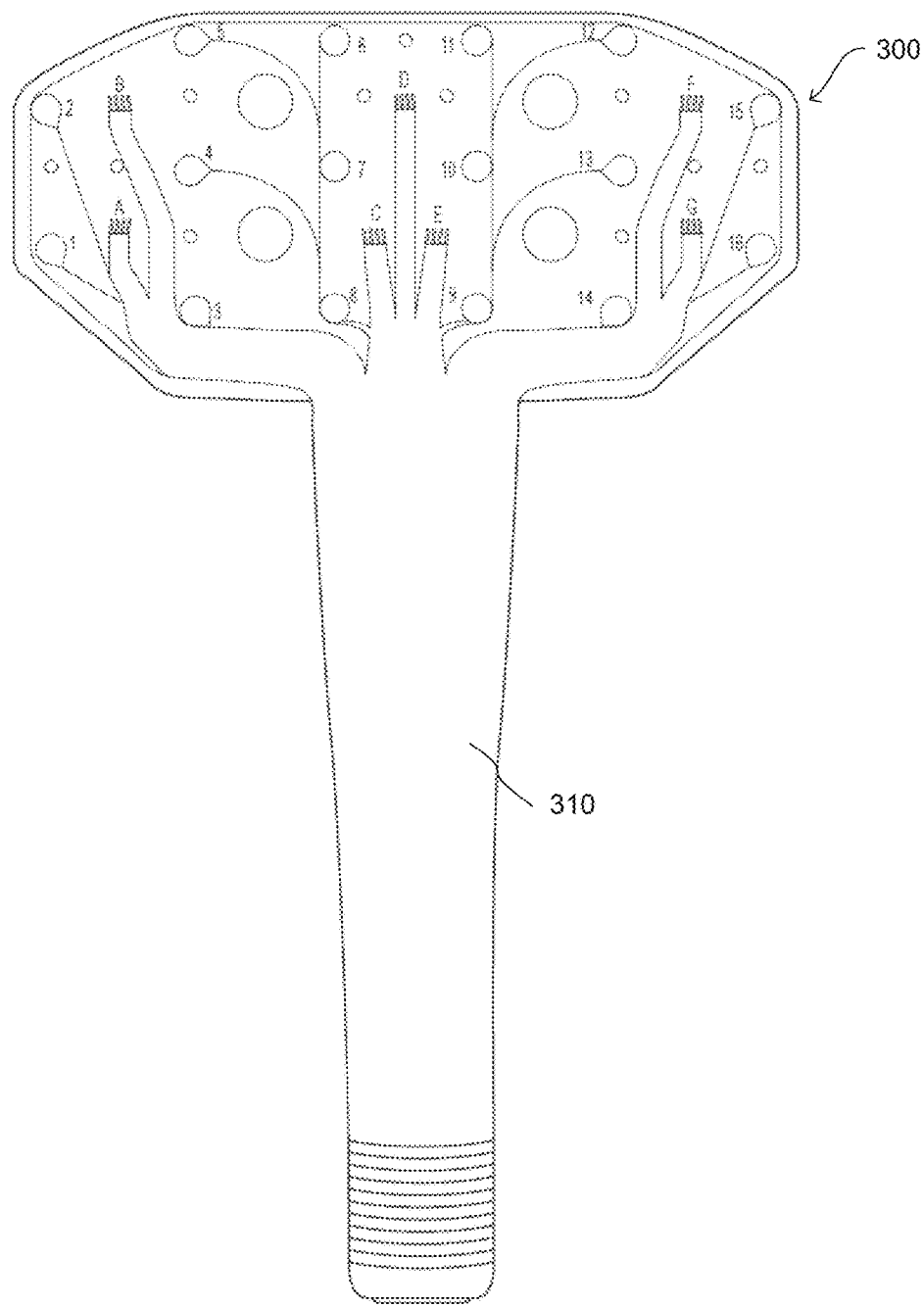
FIG. 3A illustrates an intracranial electrode grid in accordance with an example.

FIG. 3A illustrates an intracranial electrode grid 300. The intracranial electrode grid 300 can be an integrated macro and micro electrode grid. In other words, the intracranial electrode grid 300 can include a mixture of micro signal channels/sites and macro signal channels/sites. In one configuration, the intracranial electrode grid 300 can include four 4×4 micro channels/sites and 64 macro channels/sites. The four four-by-four micro channels/sites can be approximately 50 micrometers (μm) in size and spaced at approximately 400 μm. The 64 macro channels/sites are approximately 2000 μm in size and spaced at approximately 10,000 μm. For mapping purposes, numbers can be assigned to the micro channels/sites and alphabet letters can be assigned to the macro channels/sites. For example, the numbers 1-16 can be assigned to the micro channels/sites and the alphabet letters A-G can be assigned to the macro channels/sites. In one configuration, the intracranial electrode grid 300 can be comprised of parylene and have a thickness of approximately 20 μm.

In one example, the intracranial electrode grid 300 can include (or be attached to) a micro-ribbon cable 310. The micro-ribbon cable 310 can attach the intracranial electrode grid 300 to a subcutaneous microelectronic signal processing unit (not shown in FIG. 3A). The micro-ribbon cable 310 can include 200 millimeter (mm) long conductive traces (e.g., gold metal traces). The gold metal traces can have a resistance of less than 725 ohms (or approximately 36 ohms per centimeter). The conductive traces can be sandwiched or inserted between two parylene layers to form the micro-ribbon cable 310.

Figure 3B:
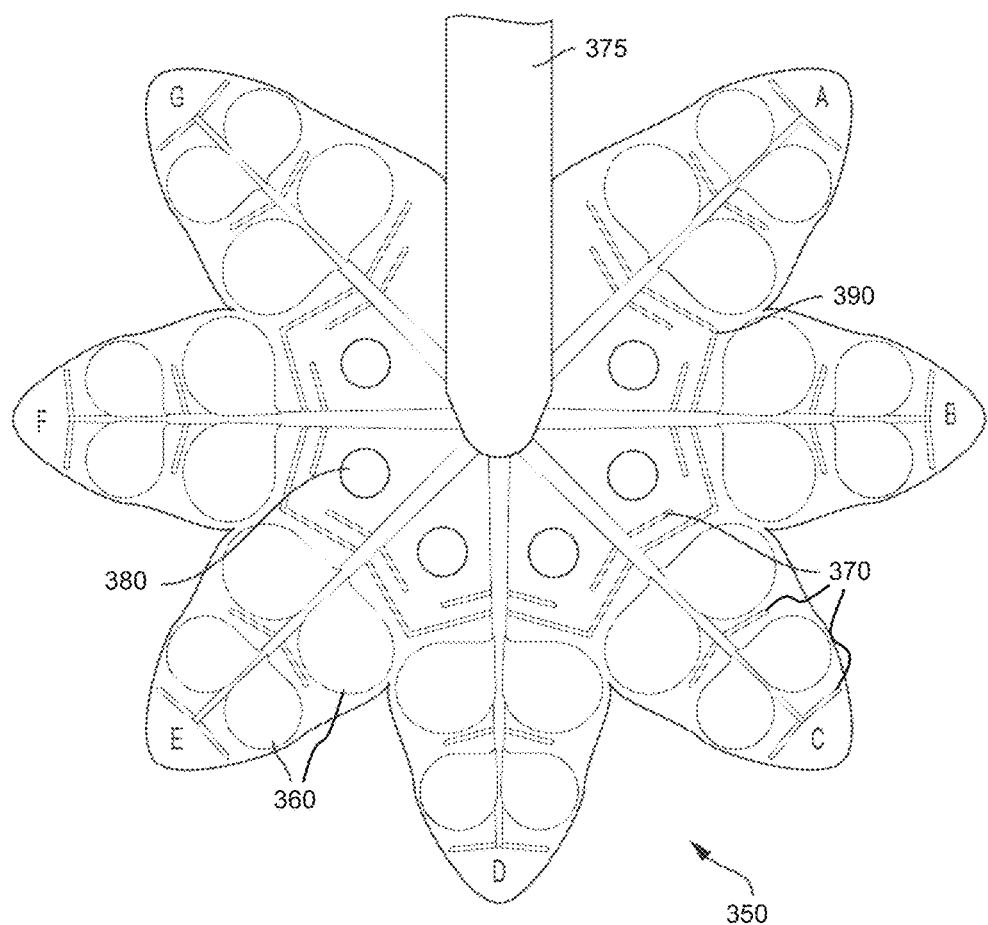
FIG. 3B illustrates an intracranial electrode grid having a hub and spoke configuration in accordance with an example.

FIG. 3B illustrates an intracranial electrode grid 350 which is similar in many respects to that shown in FIG. 3A, with the exception of having a hub and spoke or snowflake arrangement of macroelectrodes 360 and microelectrodes 370 emanating from a ribbon cable 375. In this embodiment holes 380 are also used to allow diffusion and passage of fluid across the electrode grid. In a specific example, a 128 channel, 20 μm thick Parylene-C based ECoG array was fabricated. A thin film of platinum based interconnections and sites/channels were sandwiched between two Parylene layers (5 and 15 μm respectively). In this integrated ECoG array there are overlapping micro and macro channels. There were 28 macro (diameter 2000 μm) and 100 micro (diameter 50 μm) sites/channels. The width of the ribbon cable was 250 μm. The diffusion holes were etched in the grid. A metal ring was also oriented around the perimeter of the grid as a ground and reference electrode.

FIGS. 4A-4D illustrate fabrication of an integrated intracranial electrode grid. An electrocorticography (ECoG) electrode grid array can be fabricated. The electrode grid can be parylene-based and approximately 20 μm in thickness. Thin film conductive material based interconnections and sites/channels can be sandwiched between two parylene layers (e.g., 5 μm and 15 μm in thickness). In the electrode grid array, four 4×4 micro sites/channels (50 μm in size spaced at 400 μm) and 64 macro sites/channels (2000 μm in size spaced at 10000 μm) can be fabricated. In one example, atomic layer deposition aluminum oxide (Al2O3) ultra-conformal thin films can be used as an additional encapsulation layer on the electrode grid array.

As shown in FIG. 4A, a first parylene layer 404 can be deposited over a substrate layer 402. As shown in FIG. 4B, a thin film gold layer 406 can be deposited above the parylene layer 404. Alternatively, the thin film layer 406 can be composed of other conductive materials, such as platinum, silver, copper, aluminum, zinc, nickel, iron, etc. As shown in FIG. 4C, a second parylene layer 408 can be deposited over the thin film gold layer 406 and the first parylene layer 404. As shown in FIG. 4D, the substrate layer 402 can be removed in order to produce the electrode grid array. The electrode grid array can include the thin film gold-based interconnections and sites/channels in between the first parylene layer 404 and the second parylene layer 408. In one example, the first parylene layer 404 can be 5 μm in thickness and the second parylene layer 408 can be 15 μm in thickness).

In one example, the high flexibility of the polymer/metal sandwich structure or substrate (i.e., the electrode grid array) that is immersed into a wet ionic medium can lead to an eventual delamination of the thin films. The delamination of the thin films can also result from cyclic bending. The delamination of the thin films can result because of the constant shear stress between the metal and polymer films. Deterioration and breakage of the thin film leads can also occur, thereby leading to drift of the trace impedance and eventual electrode grid array failure. In order to mitigate this problem, an additional biocompatible thin film can be deposited on the grid. The additional biocompatible thin film can be comprised of alumina oxide and be used to mitigate electrode grid array failure. As an additional safeguard, the electrode grid array can include self-testing features (e.g., impedance testing) in the ASIC, which can allow for the identification of lead and encapsulation deterioration. As a result, software applications can be run to compensate for the changes and warn patients or surgeons if the electrode grid array is reaching an end of its useful life or is losing channels.

Figure 5A:
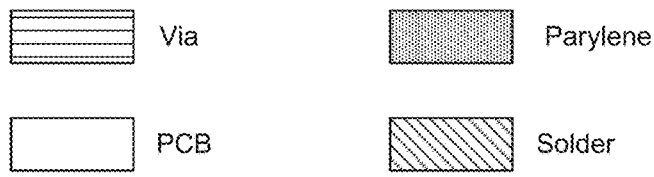
FIGS. 5A-5C illustrate fabrication of an intracranial electrode grid integrated with a subcutaneous microelectronic signal processing unit in accordance with an example.
Figure 5A:
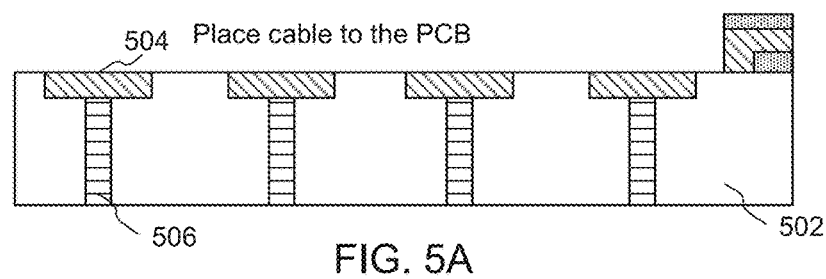
Figure 5B:
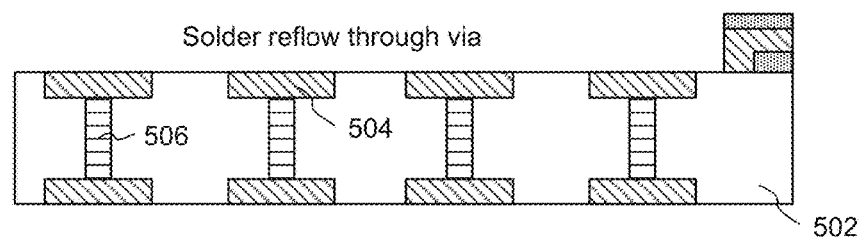
Figure 5C:
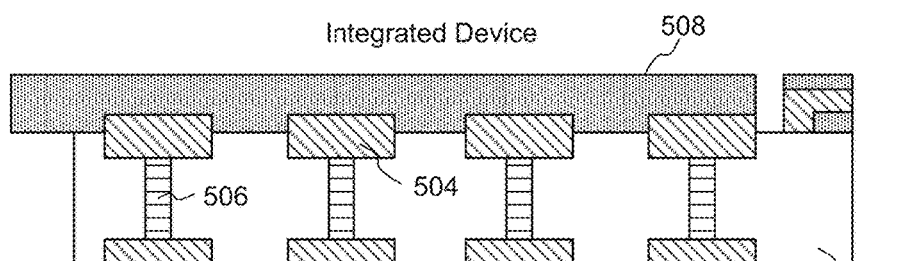

FIGS. 5A-5C illustrate fabrication of an intracranial electrode grid integrated with a subcutaneous microelectronic signal processing unit. The subcutaneous microelectronic signal processing unit can include a digital processing board (DPB) that includes a printed circuit board (PCB) 502. The intracranial electrode grid can be an electrode grid array. As shown in FIG. 5A, a wired cable or connector (e.g., a pigtail wire) can be soldered to a top side of the PCB 502. In other words, the wired cable can be connected to a first surface of the subcutaneous microelectronic signal processing unit. As shown in FIG. 5B, the PCB 502 can have small through-hole vias 506 (i.e., through holes to the other surface of the PCB), and the vias 506 can be filled with solder paste 504. In other words, solder reflow can occur through the vias 506. As shown in FIG. 5C, the electrode grid array (e.g., a parylene layer 508) can be connected to a bottom side of the PCB 502 by soldering. In other words, the electrode grid array can be connected to a second surface of the subcutaneous microelectronic signal processing unit, wherein the first surface and the second surface are on opposite sides. Metal traces and bond pads on the thin film electrode grid array can be designed to mate with bond pad spacing on the PCB 502. The vias 506 on the PCB 502 that are filled with solder paste 504 can connect the bond pads on the electrode grid array. The top side of the PCB 502 (to which the pigtail is attached) can be on an opposite end from the electrode grid array sites/channels.

In one example, the PCB 502 can have an area of less than approximately one square inch and a thickness of less than approximately four millimeters (mm). The PCB 502 can contain an amplifier application-specific integrated circuit (ASIC) and control electronics packaged in a hermetic package. The PCB can also include a controller ASIC, which can select channels on the amplifier ASIC, control the analog-to-digital converters (ADCs), and packetize data (e.g., digital neural activity information) to send off the PCB. In one example, the data can be obtained in accordance with International Electrotechnical Commission (IEC) 60601, which is a series of technical standards for the safety and effectiveness of medical electrical equipment.

In one example, coupling power into the implanted electrode grid array reliably and efficiently without large power losses/attenuation can be challenging. The electrode grid array can be positioned closer to the source (e.g., the implantable electronics encased in a titanium can and mounted on the skull), which can result in a reduced level of noise. In addition, the integration of the electrode grid array to the implantable electronics/DPB can be challenging. Therefore, as an alternative, anisotropic thin film adhesive (ATF) can be used for attaching the electrode grid array to the PCB 502. Furthermore, the PCB 502 can be encapsulated with parylene and silicone, and then encased in housing (e.g., a titanium can).

Figure 6:
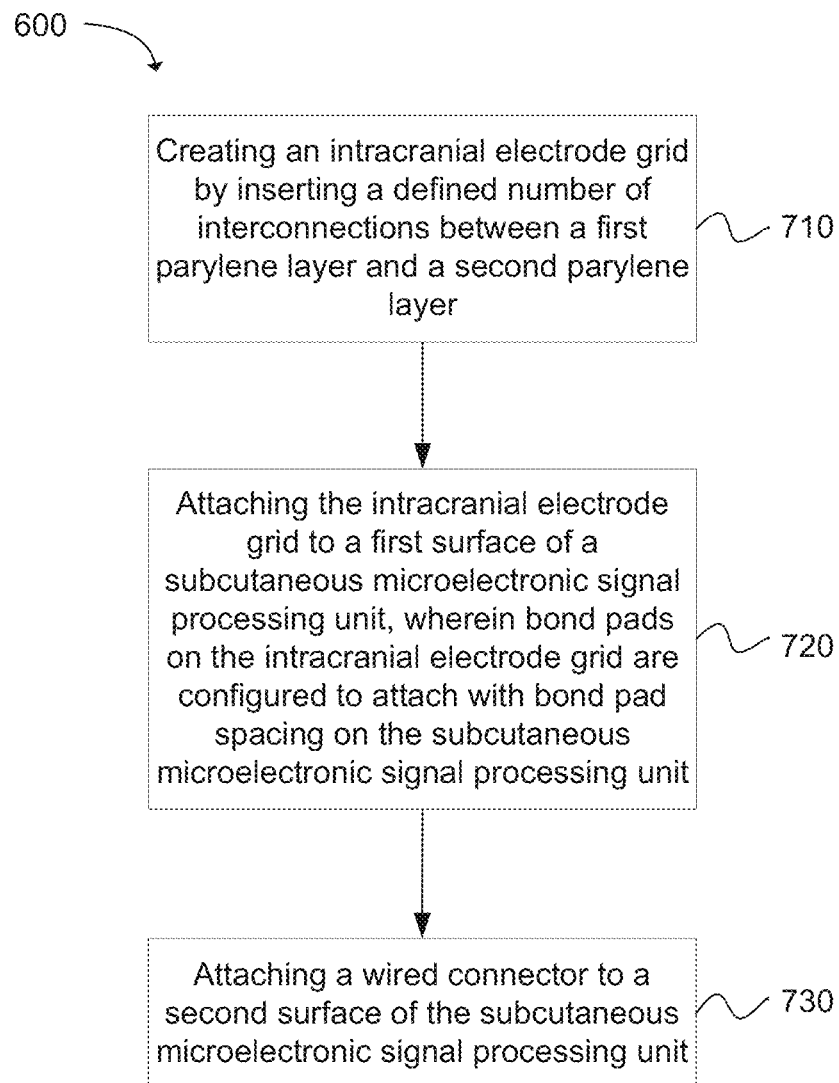
FIG. 6 depicts a flow chart of a method for manufacturing a neural interface in accordance with an example.

FIG. 6 depicts a flow chart of a method for manufacturing a neural interface. The method can include the operation of creating an intracranial electrode grid by inserting a defined number of interconnections between a first polymer layer and a second polymer layer, as in block 610. The method can include the operation of attaching the intracranial electrode grid to a first surface of a subcutaneous microelectronic signal processing unit, wherein bond pads on the intracranial electrode grid are configured to attach with bond pad spacing on the subcutaneous microelectronic signal processing unit, as in block 620. The method can include the operation of attaching a wired connector to a second surface of the subcutaneous microelectronic signal processing unit, as in block 630.

Various techniques, or certain aspects or portions thereof, may take the form of program code (i.e., instructions) embodied in tangible media, such as floppy diskettes, CD-ROMs, hard drives, non-transitory computer readable storage medium, or any other machine-readable storage medium wherein, when the program code is loaded into and executed by a machine, such as a computer, the machine becomes an apparatus for practicing the various techniques. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a RAM, EPROM, flash drive, optical drive, magnetic hard drive, or other medium for storing electronic data. The satellite may also include a transceiver module, a counter module, a processing module, and/or a clock module or timer module. One or more programs that may implement or utilize the various techniques described herein may use an application programming interface (API), reusable controls, and the like. Such programs may be implemented in a high level procedural or object oriented programming language to communicate with a computer system. However, the program(s) may be implemented in assembly or machine language, if desired. In any case, the language may be a compiled or interpreted language, and combined with hardware implementations.

It should be understood that many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. The modules may be passive or active, including agents operable to perform desired functions.

Reference throughout this specification to "an example" or "exemplary" means that a particular feature, structure, or characteristic described in connection with the example is included in at least one embodiment of the present invention. Thus, appearances of the phrases "in an example" or the word "exemplary" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as defacto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of layouts, distances, network examples, etc., to provide a thorough understanding of embodiments of the invention. One skilled in the relevant art will recognize, however, that the invention can be practiced without one or more of the specific details, or with other methods, components, layouts, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A neural interface comprising:
   an intracranial electrode grid operable to detect neural activity, wherein the intracranial electrode grid includes a macroelectrode and a microelectrode, the macroelectrode being different from the micro electrode, wherein the intracranial electrode grid is a multi-channel integrated macro and micro electrocorticography (ECoG) array system having from 8 to 1024 channels;
   a subcutaneous microelectronic signal processing unit operable to process the neural activity detected in part by the macroelectrode and the microelectrode in order to obtain digital neural activity information and multiplexing the digital neural activity information such that information received on 8 to 1024 channels can be transmitted over a cable comprising fewer channels;
   the cable connecting the intracranial electrode grid and the subcutaneous microelectronic signal processing unit; and
   a wired connector attached to the subcutaneous microelectronic signal processing unit that is operable to transmit the multiplexed digital neural activity information from the subcutaneous microelectronic signal processing unit to an external signal processing device.

2. The neural interface of claim 1, wherein the multi-channel integrated macro and micro electrocorticography (ECoG) array system having from 128 to 1024 channels.

3. The neural interface of claim 1, wherein the intracranial electrode grid is formed of a flexible bi-layer substrate surrounding electrodes, the bi-layer including an outer polymer ion barrier and an inner moisture barrier.

4. The neural interface of claim 1, wherein the cable connecting the intracranial electrode grid and the subcutaneous microelectronic signal processing unit is a micro-ribbon cable.

5. The neural interface of claim 1, further comprising a housing operable to encapsulate the subcutaneous microelectronic signal processing unit.

6. The neural interface of claim 1, wherein the subcutaneous microelectronic signal processing unit is further operable to:
   amplify the neural activity detected by the intracranial electrode grid; and
   digitize the amplified neural activity to obtain the digital neural activity information.

7. The neural interface of claim 1, wherein:
   the intracranial electrode grid adapted to be inserted within a cranial cavity; and
   the subcutaneous microelectronic signal processing unit adapted to be inserted between a cranium and a cutaneous layer.

8. The neural interface of claim 1, wherein the wired connector attached to the subcutaneous microelectronic signal processing unit is a pigtail connector adapted to exit a cutaneous layer and is connectable to the external signal processing device.

9. The neural interface of claim 1, wherein the subcutaneous microelectronic signal processing unit includes shock protection during neural interface failure.

10. The neural interface of claim 1, wherein the multichannel integrated macro and micro electrocorticography (ECoG) array system has from 256 to 1024 channels.

11. A system for detecting and processing neural activity, the system comprising:
    an integrated macro and micro electrocorticography (ECoG) array system operable to detect neural activity and having a macroelectrode and a microelectrode, the macroelectrode being different from the microelectrode, wherein the intracranial electrode grid is a multichannel integrated macro and micro electrocorticography array system having from 8 to 1024 channels;
    a subcutaneous microelectronic signal processing unit operable to process the to obtain digital neural activity information, and multiplexing the digital neural activity information such that information received on 8 to 1024 channels can be transmitted over a cable comprising fewer channels;
    the cable connecting the integrated macro and micro (ECoG) array system and the subcutaneous microelectronic signal processing unit;
    a single pigtail connector attached to the subcutaneous microelectronic signal processing unit; and
    an external signal processing device that is operable to receive the multiplexed digital neural activity information from the subcutaneous microelectronic signal processing unit via the pigtail connector.

12. The system of claim 11, wherein the integrated macro and micro electrocorticography (ECoG) array system includes from 128 to 1024 channels.

13. The system of claim 11, wherein the integrated macro and micro electrocorticography (ECoG) array system is comprised of parylene and is approximately 15 micrometers (μm) to 25 μm in thickness.

14. The system of claim 11, wherein the cable connecting the integrated macro and micro electrocorticography (ECoG) array system and the subcutaneous microelectronic signal processing unit is a biocompatible micro-ribbon cable.

15. The system of claim 11, wherein the integrated macro and micro electrocorticography (ECoG) array system includes from 256 to 1024 channels.

* * * * *